United States Patent [19]

Shichman

[11] Patent Number: 5,370,625
[45] Date of Patent: Dec. 6, 1994

[54] TROCAR GUIDE TUBE POSITIONING DEVICE

[75] Inventor: Daniel Shichman, Trumbull, Conn.

[73] Assignee: United States Surgical Corporation, Norwalk, Conn.

[21] Appl. No.: 46,785

[22] Filed: Apr. 13, 1993

Related U.S. Application Data

[60] Division of Ser. No. 861,164, Mar. 27, 1992, Pat. No. 5,217,441, which is a continuation of Ser. No. 489,482, Mar. 6, 1990, abandoned, which is a continuation-in-part of Ser. No. 394,198, Aug. 15, 1989, abandoned.

[51] Int. Cl.$^5$ .............................................. A61M 5/32
[52] U.S. Cl. ...................................... 604/174; 604/165; 604/180; 604/283; 606/185
[58] Field of Search ................ 604/161, 164, 165, 170, 604/171, 174, 180, 268, 278, 283; 606/167, 172, 181, 184, 185; 128/888

[56] References Cited

U.S. PATENT DOCUMENTS

| | | |
|---|---|---|
| 695,470 | 3/1902 | Milam . |
| 1,014,128 | 9/1912 | Crowe . |
| 1,045,906 | 12/1912 | Sweet . |
| 1,155,271 | 9/1915 | Philips . |
| 1,213,001 | 1/1917 | Philips . |
| 1,380,447 | 6/1921 | Wescott . |
| 2,001,638 | 5/1935 | Tornsjo . |
| 2,185,927 | 1/1940 | Shelanski . |
| 2,256,942 | 9/1941 | Duffy . |
| 2,338,800 | 1/1944 | Burke . |
| 2,496,111 | 1/1950 | Turkel . |
| 2,623,521 | 12/1951 | Shaw . |
| 2,705,949 | 4/1955 | Silverman . |
| 2,898,917 | 8/1959 | Wallace . |
| 2,923,295 | 2/1960 | Guerriero . |
| 2,952,256 | 9/1960 | Meader . |
| 3,030,959 | 4/1962 | Grunert . |
| 3,039,468 | 6/1962 | Price . |
| 3,241,554 | 3/1966 | Coanda . |
| 3,253,594 | 5/1966 | Matthew et al. . |
| 3,330,268 | 7/1967 | Goldsmith . |
| 3,347,232 | 10/1967 | Ginsburg . |
| 3,459,175 | 8/1969 | Miller . |
| 3,459,189 | 8/1969 | Alley . |
| 3,515,137 | 6/1970 | Santomieri . |
| 3,570,498 | 3/1971 | Weighton . |
| 3,605,752 | 9/1971 | Schlesinger . |
| 3,613,684 | 10/1971 | Sheridan . |
| 3,683,911 | 8/1972 | McCormick . |
| 3,726,522 | 4/1973 | Silberman ........................ 272/84 |

(List continued on next page.)

FOREIGN PATENT DOCUMENTS 0232600 8/1987 European Pat. Off. .

(List continued on next page.)

OTHER PUBLICATIONS

Excerpts from "1988 Orthopedics-Richards Annual Product Catalog" copyright Richards Medical Company 1988.

(List continued on next page.)

Primary Examiner—C. Fred Rosenbaum
Assistant Examiner—Corrine Maglione

[57] ABSTRACT

A trocar penetration depth indicator has a first, inner housing including a first threaded section and longitudinally extending gripping fingers, and a second, outer housing including a camming surface and a second threaded section to engage the first threaded section. The first and second housings slidably mount onto a trocar tube and can be secured relative to the guide tube by rotatably tightening the housings to cause the gripping fingers to firmly grip the trocar tube. Depth penetration indicia is provided on the guide tube surface and sufficient guide tube grasping force is obtained to prevent the depth indicator from being dislodged during trocar insertion. A guide tube positioning device is provided to engage the penetration depth indicator and to secure the guide tube relative to the surrounding skin of the patient in order to prevent inadvertent withdrawal or further insertion of the trocar.

7 Claims, 10 Drawing Sheets

U.S. PATENT DOCUMENTS

| | | |
|---|---|---|
| 3,750,667 | 8/1973 | Pshenichny . |
| 3,789,852 | 2/1974 | Kim . |
| 3,809,095 | 5/1974 | Cimber . |
| 3,817,250 | 6/1974 | Weiss . |
| 3,817,251 | 6/1974 | Hasson . |
| 3,824,556 | 7/1974 | Berkovits .................. 339/268 |
| 3,860,006 | 1/1975 | Patel . |
| 3,884,220 | 5/1975 | Hartnett . |
| 3,886,946 | 6/1975 | Hyde . |
| 3,993,079 | 11/1976 | Henriques de Gatztanondo . |
| 4,077,412 | 3/1978 | Moossun . |
| 4,177,814 | 12/1979 | Knepshield . |
| 4,186,750 | 2/1980 | Patel . |
| 4,215,699 | 8/1980 | Patel . |
| 4,230,123 | 10/1980 | Hawkins . |
| 4,299,230 | 11/1981 | Kubota . |
| 4,360,025 | 11/1982 | Edwards . |
| 4,419,094 | 12/1983 | Patel . |
| 4,516,968 | 5/1985 | Marshall et al. .................. 604/174 |
| 4,519,793 | 5/1985 | Galindo . |
| 4,533,349 | 8/1985 | Bark . |
| 4,535,773 | 8/1985 | Yoon . |
| 4,583,977 | 4/1986 | Shishov et al. . |
| 4,593,681 | 6/1986 | Soni . |
| 4,601,710 | 7/1986 | Moll . |
| 4,627,838 | 12/1986 | Cross et al. . |
| 4,648,391 | 3/1987 | Ellis . |
| 4,654,030 | 3/1987 | Moll . |
| 4,668,222 | 5/1987 | Poirier . |
| 4,670,008 | 6/1987 | Von Albertini . |
| 4,717,385 | 1/1988 | Cameron et al. . |
| 4,755,173 | 7/1988 | Konopka et al. .................. 604/167 |
| 4,767,411 | 8/1988 | Edmunds . |
| 4,772,261 | 9/1988 | Von Hoff et al. . |
| 4,838,881 | 1/1989 | Bennett .................. 604/280 |
| 4,886,502 | 12/1989 | Poirier et al. . |
| 4,894,052 | 1/1990 | Crawford . |
| 4,897,081 | 1/1990 | Poirier et al. . |
| 4,926,860 | 5/1990 | Stice et al. . |
| 4,927,421 | 5/1990 | Goble et al. . |
| 4,976,697 | 12/1990 | Walder et al. . |
| 4,978,342 | 12/1990 | Heimreid . |
| 4,985,019 | 1/1991 | Michelson . |
| 5,000,741 | 3/1991 | Kalt . |
| 5,002,557 | 3/1991 | Hasson . |
| 5,009,227 | 4/1991 | Nieuwstad .................. 128/207.17 |
| 5,009,643 | 4/1991 | Reich et al. .................. 604/165 |
| 5,073,169 | 12/1991 | Raiken .................. 604/180 |
| 5,112,321 | 5/1992 | Hiltebrandt . |
| 5,135,506 | 8/1992 | Gentelia et al. . |
| 5,137,520 | 8/1992 | Maxson et al. . |
| 5,176,648 | 1/1993 | Holmes et al. .................. 604/164 |
| 5,195,981 | 3/1993 | Johnson . |
| 5,224,935 | 7/1993 | Hollands . |
| 5,226,890 | 7/1993 | Ianniruberto et al. . |
| 5,267,970 | 12/1993 | Chin et al. . |

FOREIGN PATENT DOCUMENTS

| | | |
|---|---|---|
| 232600 | 8/1987 | European Pat. Off. . |
| 949943 | 9/1949 | France . |
| 475215 | 10/1952 | Italy . |
| 921554 | 4/1982 | U.S.S.R. . |

OTHER PUBLICATIONS

Bone Screw Technical Information, copyright Richards Manufacturing Company, Inc., 1980.

"ENDOPATH" Instructions for Use, Ethicon, Inc. copyright 1989 and photo of ENDOPATH 5 mm trocar.

Karl Storz Endoskope, "Trocars, Size:5.5 mm.–Double Puncture Approach," single sheet of promotional literature.

Karl Storz Endoskope, "For Open Laparoscopy," single sheet of promotional literature.

"5 mm–Instrumente/5 mm Instruments," single sheet of promotional literature.

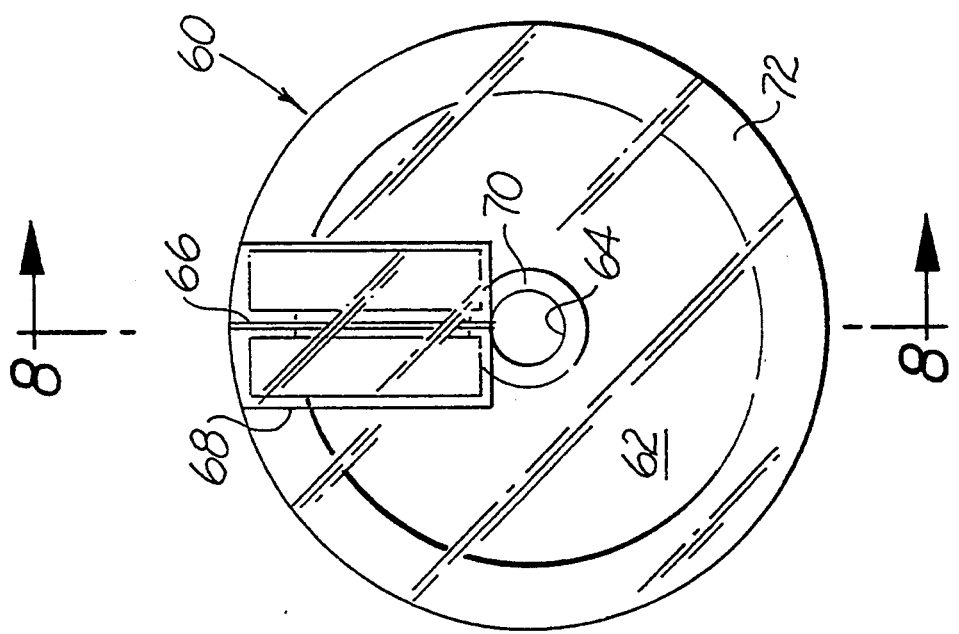
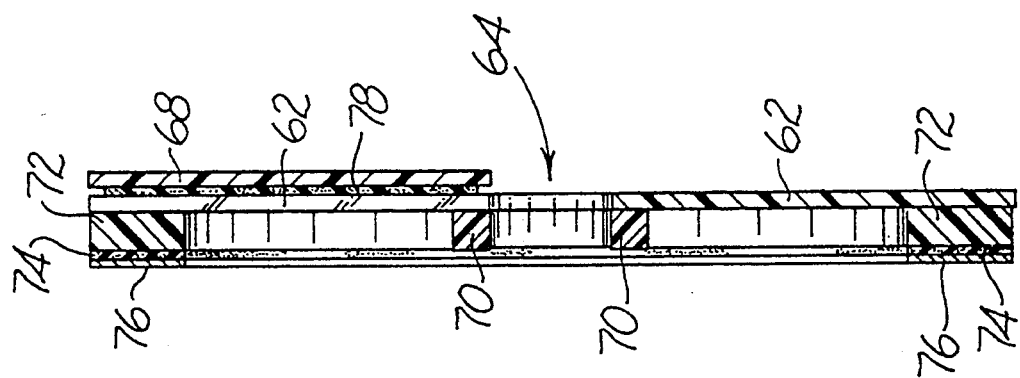

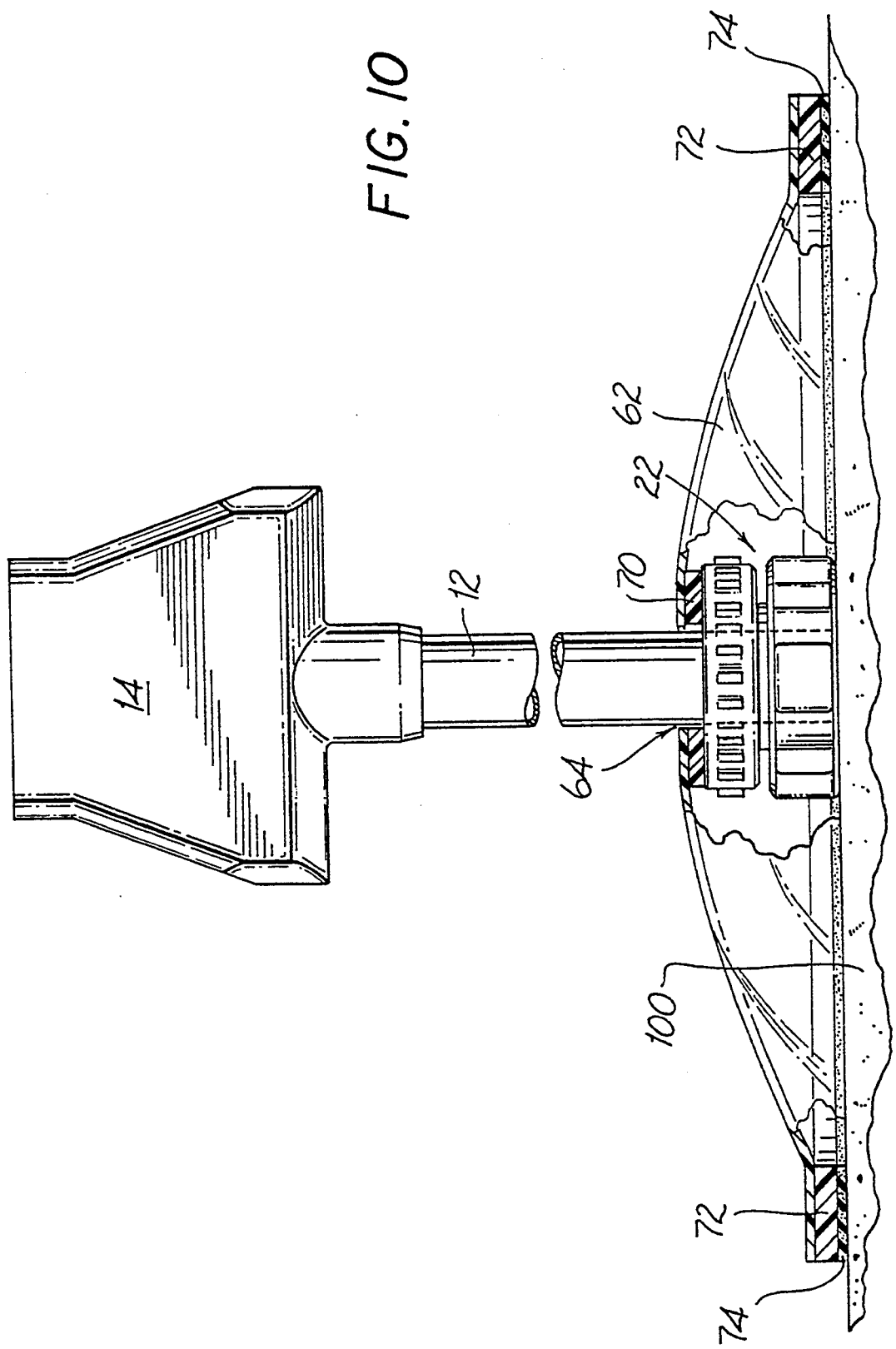

TROCAR GUIDE TUBE POSITIONING DEVICE

This is a division of U.S. application Ser. No. 07/861,164 filed Mar. 27, 1992; now U.S. Pat. No. 5,217,441 which is a continuation of application Ser. No. 07/489,482, filed Mar. 6, 1990 now abandoned, which is a continuation-part of application Ser. No. 07/394,198, filed Aug. 15, 1989 now abandoned.

TECHNICAL FIELD

The present invention relates generally to a trocar and, more specifically, to improvements for indicating the penetration depth of a trocar and for maintaining the position of the inserted trocar guide tube relative to the body.

BACKGROUND AND OBJECTS OF THE INVENTION

Trocars of the type relating to the present invention generally include a stylet having a sharp tip for penetrating through a patient's abdominal wall or other body cavity, a protective shield tube surrounding the stylet, and an outer guide tube surrounding the protective shield tube. Typically, the protective shield tube and stylet extend beyond the distal end of the guide tube, and the protective tube is spring-biased in a locked distal position surrounding the sharp tip of the styler. To use the trocar, the protective tube is unlocked so that the protective tube moves proximally to expose the stylet tip for penetrating the abdominal wall. Once the abdominal wall has been penetrated, the protective tube slides distally under the force of the spring to again assume the locked, distal position covering over the sharp stylet tip. In this manner the outer guide tube is placed into the body at a desired location. Thereafter, the styler and protective tube may be removed to leave the guide tube in place. Trocars of this type are generally described in Moll U.S. Pat. Nos. 4,601,710 and 4,654,030. After the guide tube has been placed within the body, surgical instruments may be inserted through the guide tube.

Unfortunately, known trocars do not provide any indication of trocar penetration depth to the surgeon, who must estimate the penetration depth during and after penetration of the abdominal wall. Some surgeons accomplish this task by simply resting a finger on the outer guide tube as a visual aid during insertion. Of course, this approach is unreliable, since the surgeon's finger is, at best, a rough approximation of penetration depth. Moreover, the surgeon's finger is susceptible to slipping or moving during insertion of the trocar.

Numerous penetration indicating and limiting devices have heretofore been proposed in relation to various types of surgical devices and instruments. These include graduated scales or other marks, see, for example, U.S. Pat. Nos. 3,459,189 and 3,993,079, and collar-type devices with a set or fixing screw bearing against the apparatus to be inserted, see, for example, U.S. Pat. Nos. 1,213,001 and 2,496,111 and Italian Patent No. 475215. Unfortunately, in the context of a trocar, merely providing a graduated scale or mark would be inadequate since this requires conscious visual attention of the surgeon or an attendant during insertion and provides no protection against over insertion during initial penetration. Moreover, the indicia on the graduated scale or marker may become obscured under surgical conditions, and constant attention to the scale is not possible. Set or fixing screws pose the undesirable possibility that overtightening may dent or damage the device. In the case of modern trocars, such damage could impair the structural integrity of the trocar guide tube and/or interfere with the operation of instruments inserted into the body through the trocar guide tube. Even relatively minor damage to a trocar guide tube may alter the relatively small internal diameter of the tube, e.g., on the order of about 10 millimeters or less, and interfere with insertion, rotation, or operation of sophisticated medical instruments designed to operate closely within the limited trocar guide tube space.

U.S. Pat. No. 3,817,250 discloses a collar for limiting penetration of a tracheostomy device. However, that device permits penetration to only one preset depth and undesirably obscures the insertion site.

U.S. Pat. No. 3,613,684 discloses a trocar catheter having a depth penetration limiting device consisting of a slotted tubular member with a slotted, radially extending collar. In use, the limiting device is grasped to isolate the device relative to the catheter shaft during insertion. Unfortunately, it appears the depth penetrating device may slip accidentally during insertion if not grasped firmly and constantly. In addition, the device there disclosed apparently requires an inconvenient two-handed penetration technique. This would seem to require an extended trocar shaft to allow sufficient room to grasp the shaft during penetration.

Other penetration depth indicators rely upon pressure sensitive devices. These include U.S. Pat. Nos. 2,623,512; 4,186,750; and 4,215,699 and Russian Patent 921554.

Notwithstanding the foregoing disclosures, there presently exists a need for trocar penetration depth indicator which provides convenient, reliable indication of trocar penetration depth during and after one-handed insertion of a trocar, and which does not unduly lengthen the trocar guide tube or present a hazard of damaging the guide tube by overtightening a set or fixing screw.

Once penetration of the body wall has been attained, the stylet is removed, leaving a guide tube penetrating the body adapted to receive surgical instruments. However, the guide tube may be subject to unintentional and undesirable changes in penetration depth or accidental withdrawal from the body. Therefore, there also exists a need for a positioning device to hold the guide tube at the desired penetration depth during use. At the same time, however, the positioning device should accommodate manipulation of the guide tube by the surgeon during the surgical procedure.

Accordingly, it is one object of the present invention to provide a trocar depth indicator.

A further object of the present invention is to provide a trocar depth indicator which does not limit the useful penetration length of existing trocars or require undue extension of the trocar barrel length.

Another object of the present invention is to provide a trocar penetration depth indicator which may be securely positioned relative to the trocar guide tube so as to reduce the likelihood of displacement of the depth indicator along the guide tube during penetration.

It is yet a further object of the invention to provide a trocar depth indicator which may be positioned relative to the trocar guide tube without damaging the guide tube or interfering with the operation of delicate instruments inserted therethrough.

Yet another object of the present invention is to provide a trocar guide tube positioning device for positioning the inserted trocar guide tube relative to the body.

These and other objects and advantages are accomplished in a compact, lightweight and low cost device which provides reliable indication of trocar penetration depth without unduly obstructing the trocar guide tube, and which positions the inserted trocar guide tube relative to the body to prevent accidental removal of the trocar or inadvertent changes in penetration depth.

SUMMARY OF THE INVENTION

In accordance with the present invention, a trocar penetration depth indicator is provided having inner and outer housings threadingly coupled to one another.

The inner housing includes an inner housing body having a hand grip portion, a threaded portion and a plurality of distally extending gripping fingers. An axial cylindrical opening through the inner body housing has a minor diameter defined by the proximal end of the gripping fingers configured and dimensioned to conform closely to the outer diameter of a trocar guide tube.

The outer housing includes an outer housing body having a hand grip portion, a threaded portion, and a camming surface adjacent a cylindrical axial aperture. The outer housing is configured and dimensioned so that the outer housing threaded portion may engage the inner housing threaded portion and the outer housing camming surface may engage the inner housing gripping fingers.

In use, the inner and outer housings may be loosely assembled together without tightening the threaded coupling therebetween. So assembled, the penetration depth indicator may be mounted over the trocar guide tube. In this first, untightened position, the trocar depth indicator may be slid along the guide tube to a desired position. Preferably, the inner housing gripping fingers are configured and dimensioned so that, even in the first, unlocked position, the depth indicator frictionally engages the outer surface of the trocar guide tube and will remain in place until moved to a different position.

Once positioned on the guide tube, the inner or outer housings, or both, are rotated relative to one another in order to cause the depth indicator to assume a second, tightened position. In the tightened position the outer housing camming surface exerts radially inward pressure on the inner housing gripping fingers in order to establish sufficient frictional engagement between the gripping fingers and guide tube to prevent movement of the depth indicator relative to the guide tube during insertion and use of the trocar. Preferably, graduated markings are provided on the outer surface of the guide tube which indicate the approximate penetration depth. Of course, the trocar depth indicator can repeatedly be unlocked and locked to adjust the position along the guide tube.

Advantageously, the gripping fingers establish a substantially uniform distribution of gripping forces around the guide tube, thereby preventing damage to the guide tube which might otherwise occur in connection with exertion of equivalent forces over a much smaller area, i.e., by a set screw. Remarkably, however, the gripping forces of the tightened depth indicator on the guide tube are sufficient to withstand substantial forces without the depth indicator being displaced along the guide tube. A further surprising advantage of the invention is that the present trocar depth indicator is very compact, occupying a very short length of the guide tube. Consequently, the depth indicator does not reduce the available penetration length of the trocar during use. Indeed, in the preferred embodiment the housing of the penetration depth indicator proximal to the trocar guide tube housing is configured and dimensioned to receive and nest over the guide tube collar on the guide tube housing, thereby maximizing the effective useful length of existing trocars without modification.

In a further preferred embodiment, a guide tube positioning device is provided for positioning the guide tube relative to the body once the desired penetration depth has been achieved. The positioning device may constitute a generally circular skirt made of a clear plastic material. The skirt has an axial aperture configured and dimensioned to receive the trocar guide tube, a first foam pad ring adhered to the distal side of the skirt surrounding the skirt aperture, and a second, circumferential foam pad ring adhered to the distal side of the skirt at the periphery thereof. The distal side of the second ring is provided with an adhesive covered by a release sheet. A radial slit through the skirt and first and second rings extends from the skirt aperture to the peripheral edge of the skirt, and a latch member is provided for joining the edges of the radial slit.

In use, the trocar guide tube is inserted at a point proximal to the penetration depth indicator through the radial slit so that the guide tube is disposed in the skirt aperture with the skirt proximal to the penetration depth indicator. The latch member closes the radial slit and the release sheet is removed from the second annular ring to adhere the same to the surrounding skin of the patient. The first foam pad ring contacts the proximal surface of the penetration depth indicator, such that the penetration depth indicator prevents further penetration of the trocar guide tube, and the skirt prevents accidental withdrawal of the trocar from the desired penetration depth.

Alternatively, the positioning device may constitute a sleeve member integral with the depth indicator having radially projecting rib members which engage the patient's skin at the incision when the sleeve is inserted into the incision.

It will be understood by those skilled in the art that the foregoing general description and the following detailed description are exemplary and explanatory of the invention but arc not restrictive thereof.

BRIEF DESCRIPTION OF THE DRAWINGS

The accompanying drawings, referred to herein and constituting a part hereof, illustrate preferred embodiments of the present invention, and together with the description, serve to explain the principles of the invention.

FIG. 7 is a proximal end view of the guide tube positioning skirt in accordance with the invention;

FIG. 8 is a cross-section view of the guide tube positioning skirt taken along lines 8—8 of FIG. 7;

FIG. 10 is an elevation view of the penetration depth indicator and guide tube positioning skirt illustrating a trocar guide tube positioned relative to a patient's body.

DETAILED DESCRIPTION OF THE PREFERRED EMBODIMENTS

Figure 1:
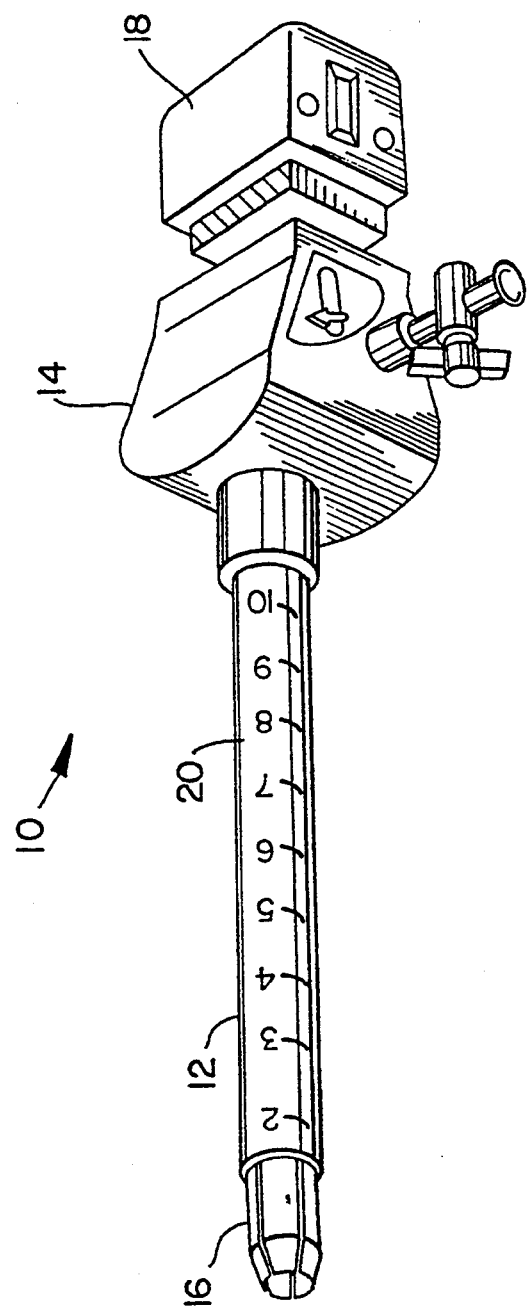
FIG. 1 is a perspective view of a trocar of the type relating to the present invention, illustrating a graduated depth penetration scale on the guide tube.

Referring now to FIG. 1, there is shown a trocar 10 having a guide tube 12 extending distally from a guide tube housing 14, and a stylet protective shield tube 16 slidably mounted within guide tube 12 and supported by a stylet housing 18. Styler housing 18 also supports a sharp-tipped stylet (not shown) disposed within protective tube 16. Generally, protective tube 16 is spring biased and locked in the extended position shown in FIG. 1 prior to use. In order to use the trocar, guide tube housing 14 and styler housing 18 are urged together to unlock protective tube 16, and the tip of the trocar is pressed against the patient's body. As the trocar tip is pressed against the body, the protective tube is urged proximally within the guide tube to reveal the sharp styler for penetration of the body wall. After penetration, the protective tube returns to the extended locked position shown in FIG. 1. In this manner, the guide tube is inserted into the patient's body and may be maneuvered to the desired point. The guide tube, with the stylet and protective tube removed, provides access for viewing and/or performing surgery within the body without a traditional incision. The guide tube is held in place by the guide tube positioning skirt (see FIG. 10) or sleeve (see FIG. 11). Preferably, the guide tube and/or guide tube housing at all times provide a seal between the penetrated body cavity and the external atmosphere. As shown in FIG. 1, in accordance with the invention, guide tube 12 is preferably provided with penetration depth indicia, shown in the form of a graduated scale 20, the purpose of which shall become apparent below.

Figure 2:
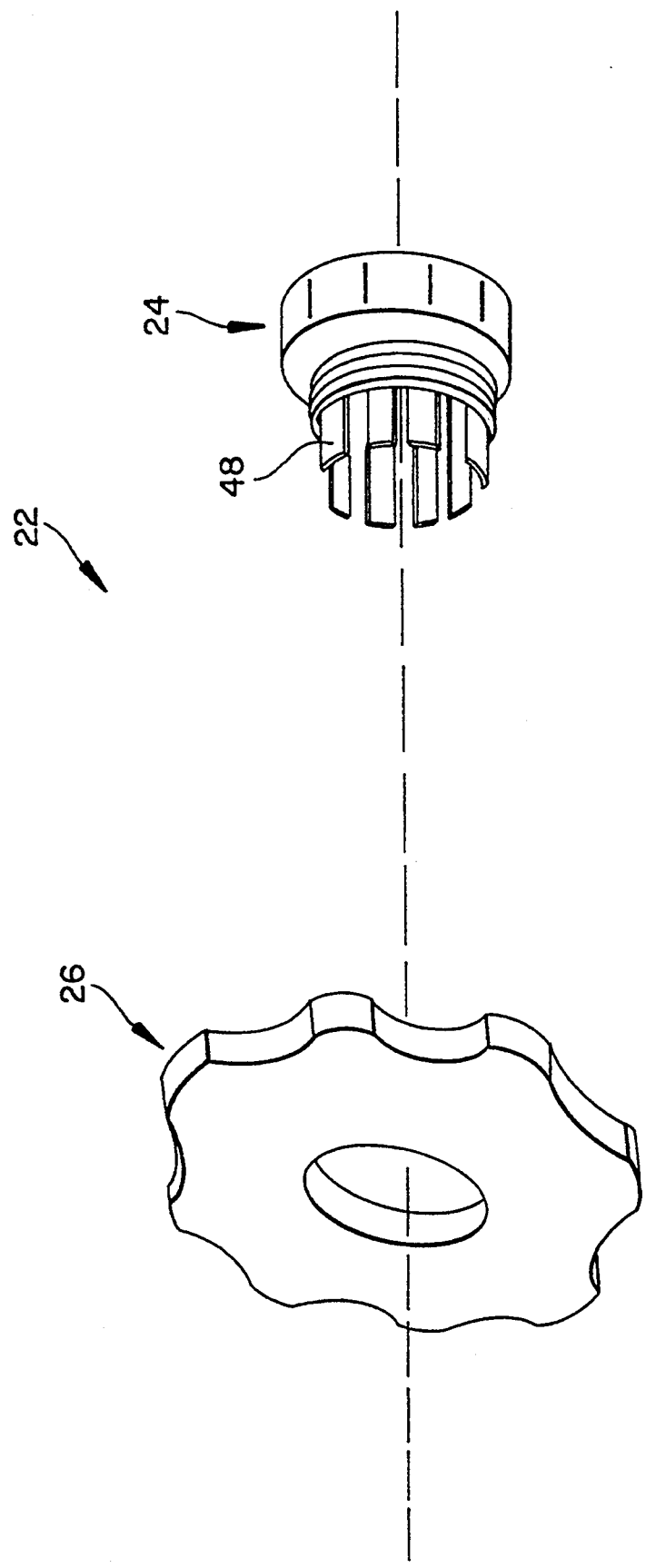
FIG. 2 is a perspective view of the unassembled trocar penetration depth indicator of the present invention.
Figure 3:
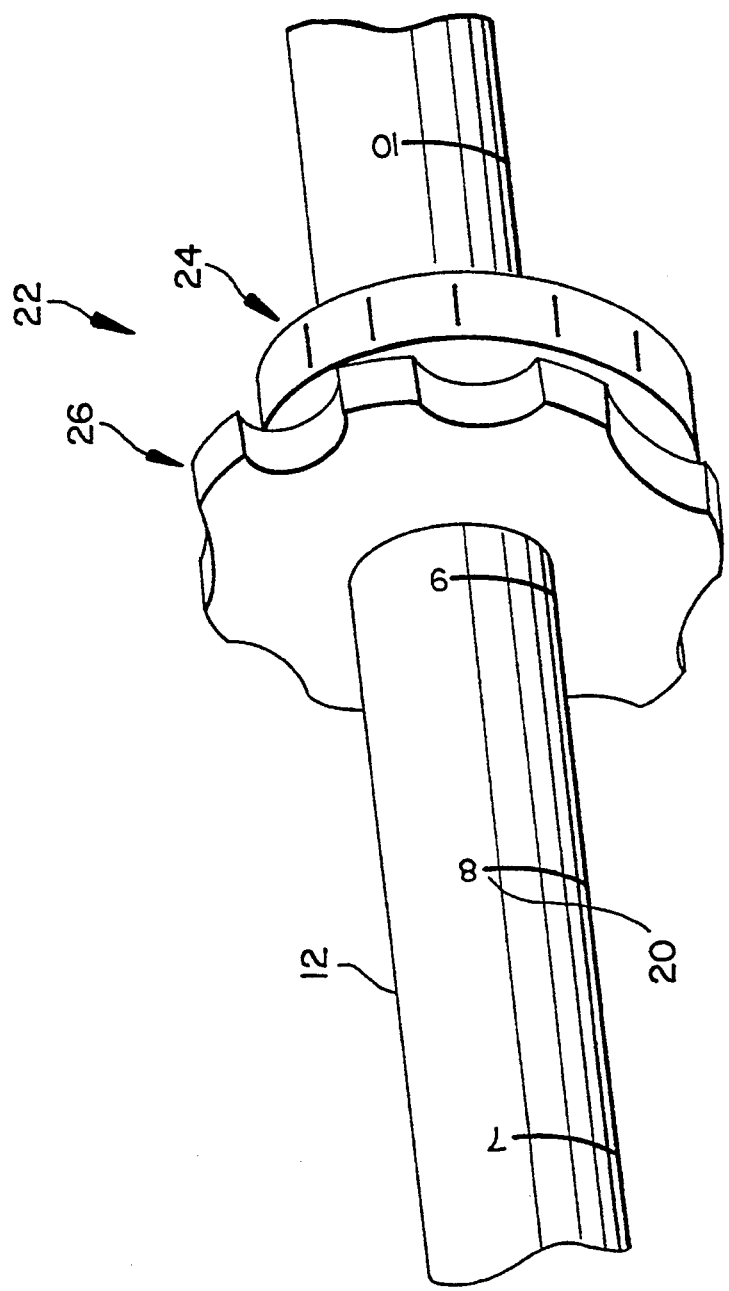
FIG. 3 is a perspective view of the penetration depth indicator mounted on the trocar guide tube.

FIGS. 2 and 3 illustrate the trocar penetration depth indicator of the present invention generally denominated by numeral 22 including a first, inner housing 24 and a second, outer housing 26. The first and second housings have axially aligned apertures to receive guide tube 12. The inner and outer housings rotatably engage to assume an unlocked position wherein the trocar penetration depth indicator may be slidably urged along guide tube 12 to a desired position. After the desired position has been attained, the inner and outer housings are rotated relative to one another so that a camming surface on the outer housing constricts a plurality of gripping fingers 28 on the inner housing to frictionally engage and grasp the guide tube, thereby preventing further sliding motion of the depth indicator relative to the guide tube.

Figure 4B:
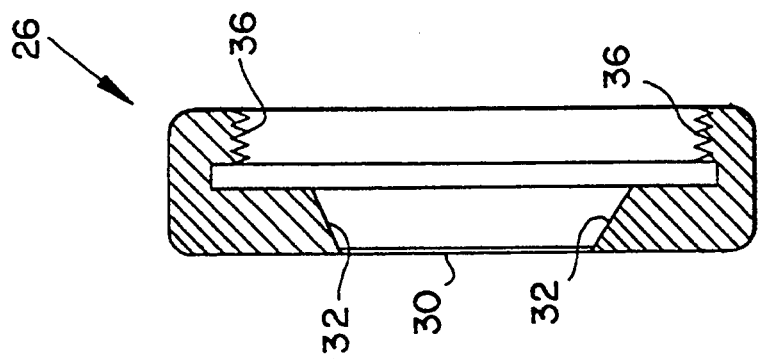
FIG. 4B is a cross-section view of the outer housing taken along lines 4—4 of FIG. 4A.
Figure 4A:
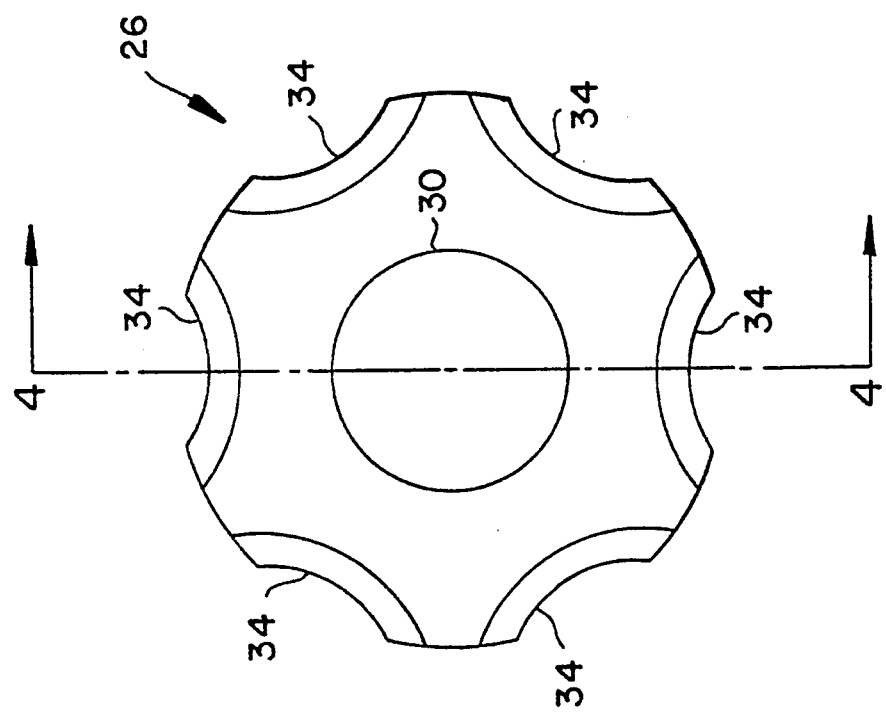
FIG. 4A is a distal end view of the outer housing of the penetration depth indicator shown in FIGS. 2 and 3.

FIG. 4A is a distal end view of outer housing 26. As there shown, outer housing 26 is generally cylindrical, with a central aperture 30 and a gripping portion along the outer circumference of the housing. Preferably, the gripping portion includes a number of finger accommodating depressions 34. FIG. 4B is a cross-section view of outer housing 26 taken along line 4—4 of FIG. 4A. As shown in FIG. 4B, outer housing 26 further includes a distally inwardly inclined camming surface 32 adjacent aperture 30 and an inwardly facing outer housing threaded section 36. It will be noted that the outer housing has a substantially open center with the smallest diameter of the outer housing defined by aperture 30 adjacent camming surface 32. By way of example only, the outer housing may be constructed, such as by molding, of glass filled acetal or polycarbonate. Preferably, the outer housing is constructed of glass-filled acetal. One appropriate acetal material is available from LNP Division of ICI America Inc. under the trade specification KFL 4023.

Figure 5B:
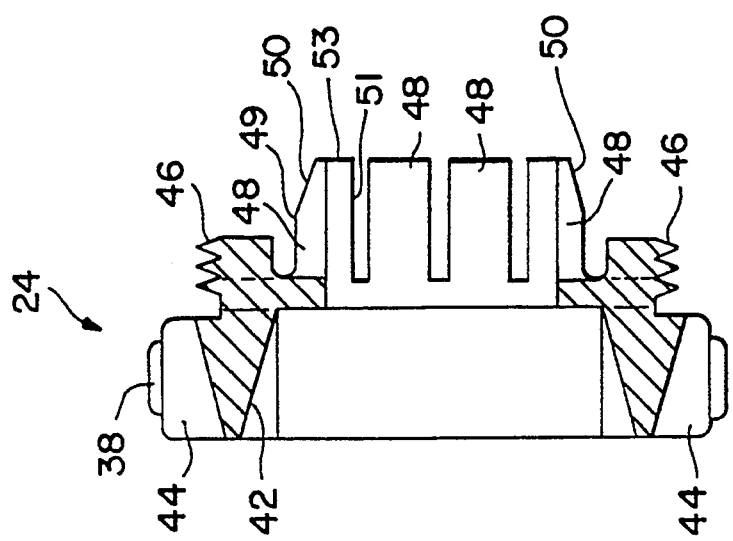
FIG. 5B is a cross-section view of the inner housing taken along lines 5—5 of FIG. 5A.
Figure 5A:
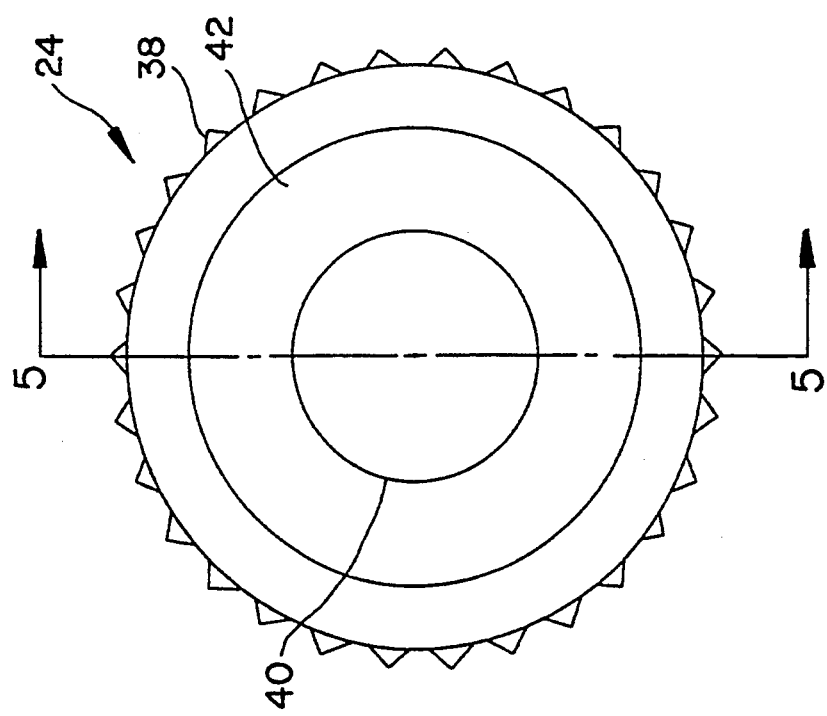
FIG. 5A is a proximal end view of the inner housing of the penetration depth indicator shown in FIGS. 2 and 3.
Figure 5C:
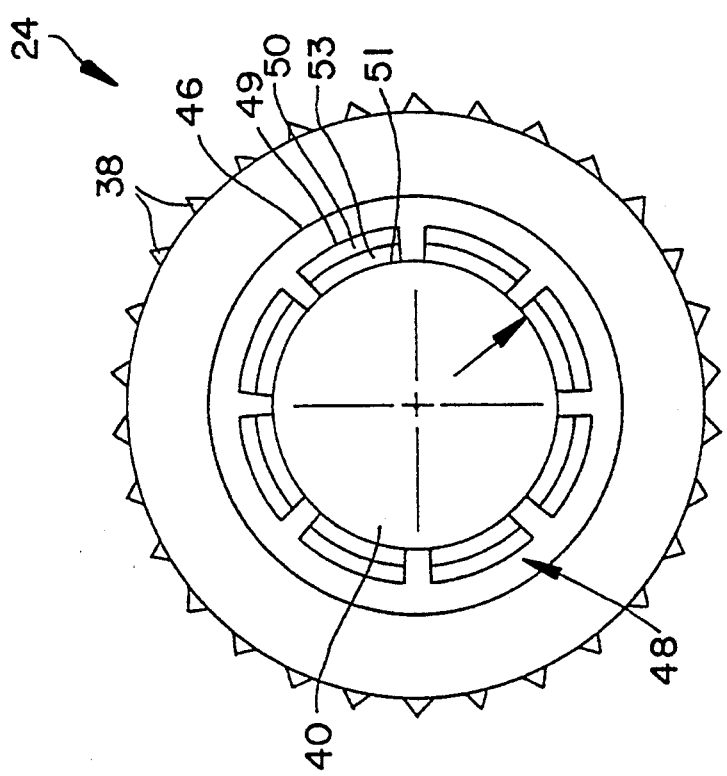
FIG. 5C is a distal end view of the inner housing shown in FIGS. 5A and 5B.

FIG. 5A is a proximal end view of inner housing 24 showing gripping projections 38 disposed on the outer circumference of flange 37 the inner housing. Also shown are a central aperture 40 and a nesting area 42 for accommodating a portion of the guide tube housing. FIG. 5B is a cross-section view of inner housing 24 taken along lines 5—5 of FIG. 5A. As there illustrated, the inner housing is generally cylindrical and includes a gripping portion 44 supporting gripping projections 38. The inner housing also has an outwardly facing threaded section 46 to engage outer housing threaded section 36, and a number of longitudinally extending gripping fingers 48 for frictionally gripping the trocar guide tube under constriction of the outer housing. Each gripping finger has an outer surface 49, an inner surface 51 and a distal end surface 53. Preferably, an inclined gripping finger camming surface 50 is provided between the outer gripping finger surface 49 and distal end surface 53. As explained more fully below, gripping finger camming surface 50 engages the outer housing camming surface 32 to ensure uniform, radially-inward constriction of the gripping fingers to grip the guide tube. Nesting area 42 is illustrated in FIG. 5B as an inclined surface of distally decreasing diameter. The increased proximal open area obtained by the inclined surface of nesting area 42 accommodates a portion of the guide tube housing (see FIG. 6). Of course, the nesting area could also take other forms, such as an area of uniform enlarged diameter sufficient to accommodate the guide tube housing. FIG. 5C, a distal end view of inner housing 24, illustrates the arrangement of the gripping fingers. As shown, the inner surface 51 of each gripping finger is curved to conform to the radius of curvature of the guide tube. FIG. 5C also illustrates the preferred arrangement of eight gripping fingers. The number and specific arrangement of gripping fingers are not critical, but the preferred arrangement of a plurality of gripping fingers having concave inner surfaces advantageously distributes gripping forces about the circumferential area of contact with the trocar guide tube. By way of example only, inner housing 24 may be constructed, as by molding, of a glass filled acetal or polycarbonate. In the preferred embodiment wherein the outer housing is constructed of glass-filled acetal, the inner housing is preferably constructed of polycarbonate. One suitable polycarbonate material is available from General Electric Company under the trade name LEXAN. The preferred acetal-polycarbonate arrangement reduces binding at the threaded engagement of threaded sections 36, 46. Of course, the same result may be obtained by constructing the outer housing of polycarbonate and the inner housing of acetal, but acetal may slide on the steel cannula or guide tube.

Figure 6:
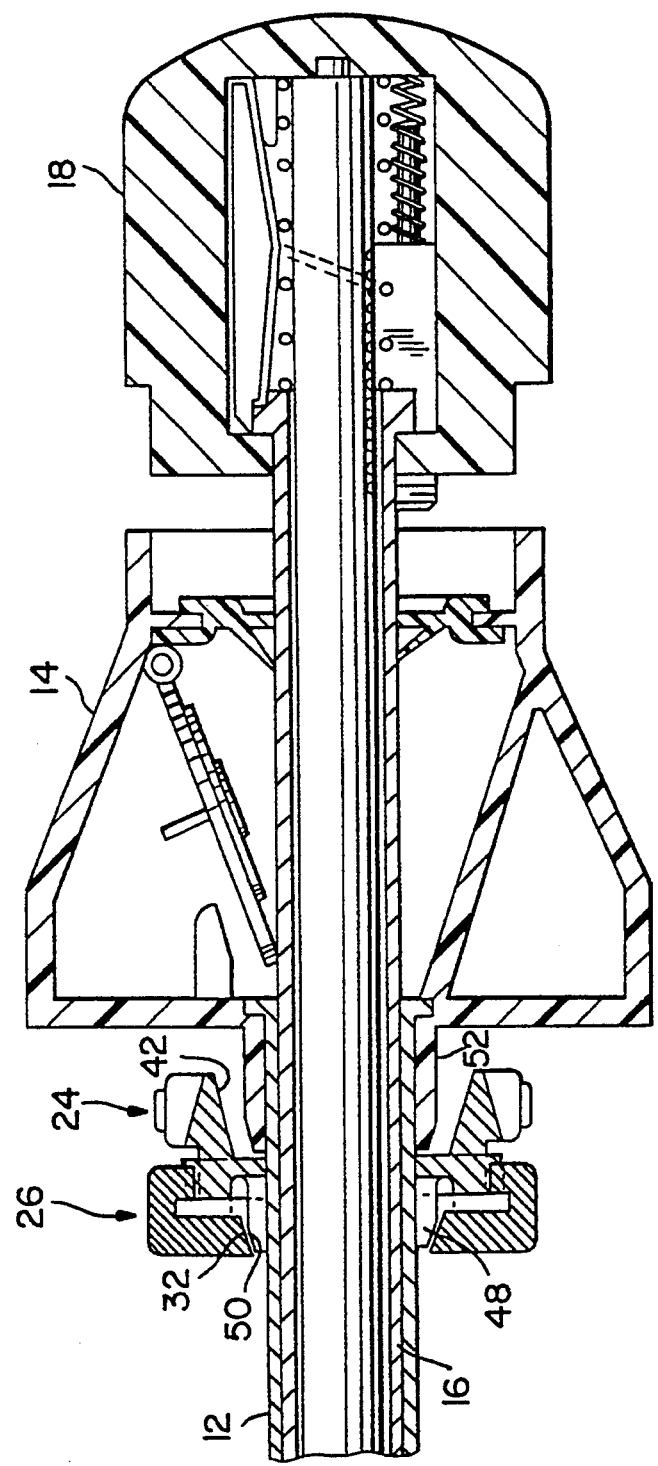
FIG. 6 is a cross-section elevation view of the depth penetration indicator mounted on the trocar guide tube and nested over a portion of the guide tube housing.

FIG. 6 shows the trocar depth indicator with inner and outer housings 24, 26 fully assembled, mounted to and gripping trocar guide tube 12. In FIG. 6, inner housing 24 is nested over the guide tube collar 52 extending from guide tube housing 14. As will be understood from the Figures, particularly FIG. 6, rotatably tightening the inner and outer housings by engagement of threaded sections 36, 46 causes the inner and outer housings to be longitudinally drawn together. As the housings are drawn together, outer housing camming surface 32 engages gripping finger camming surfaces 50 to exert radially inward force on gripping fingers 48 to securely grasp outer guide tube 12. Advantageously, the plurality of gripping fingers conforming to the guide tube surface uniformly distributes substantial frictional gripping force over virtually the entire guide tube surface. Remarkably, the present invention develops sufficient gripping force to withstand substantial force, on the order of about 25-30 pounds. However, because the gripping force is not concentrated over a small area, as in the case of a set screw, there is no danger of damaging the structural configuration of the guide tube. The depth indicator according to the present invention securely grips the guide tube and provides an indication of penetration depth which may be relied upon with reasonable confidence that the depth indicator will not accidentally be displaced from the desired position. It is also contemplated and desired that the inner and outer housings assume a first, unlocked position with the threaded sections loosely engaged to keep the housings together without constricting the gripping fingers against the guide tube. Of course, in this unlocked position the trocar penetration depth indicator may deliberately be moved along the guide tube and will remain static in any position where the indicator is disposed. The trocar penetration depth indicator is effectively secured relative to the guide tube when the inner and outer housings are rotatably tightened to assume the second, locked gripping position with the outer housing camming surface constricting the gripping fingers.

In order to obtain these desirable features, the inner housing should be configured and dimensioned so that gripping fingers 48 define an opening having a diameter slightly larger than the outer diameter of the corresponding guide tube when the gripping fingers are not constricted by the outer housing. Similarly, in order to obtain sufficient gripping force, the gripping fingers should be constricted by the outer housing so as to define an opening having a diameter conforming to the outer diameter of the guide tube. Advantageously, the maximum constriction of the gripping fingers may be limited by limiting the travel of the threaded sections of the inner and outer housings. In order to achieve the desired gripping action without overtightening, it is contemplated that the maximum tightened position of the threaded inner and outer housings should constrict the gripping fingers to a maximum constricted position to define an aperture having a diameter slightly smaller than the outer diameter of the guide tube. By way of example, but not limitation, a standard 10 millimeter trocar has a nominal inner diameter of about 10 millimeters and a nominal outer diameter of about 10.3 millimeters. Accordingly, a depth indicator of the present invention for use with a 10 mm trocar should be constructed so that the inner housing gripping fingers define an opening slightly larger than 10.3 millimeters in diameter when not constricted by the outer housing, i.e., on the order of about 10.4 or 10.5 millimeters. Conversely, the maximum constriction of the gripping fingers by the outer housing should define an aperture slightly less than about 10.3 millimeters in diameter such as From about 9.8 to 10.2 millimeters. Of course, the maximum constricted position would actually be achieved only in the absence of a guide tube, but so defining a maximum constricted position makes it impossible to overtighten the depth indicator to cause deformation of the guide tube. It will be understood by those or ordinary skill in the art that these principles also applies to depth indicators to be used with different size trocars.

In use, the trocar penetration depth indicator is mounted onto the trocar guide tube prior to use. The depth indicator, preferably disposed in the unlocked position with the inner and outer housings loosely engaged, is moved longitudinally along the guide tube to the desired penetration depth position. Advantageously, the distal surface of outer housing 26 may be used as a cursor against depth penetration indicia 20 on the guide tube surface (see FIG. 3). Once disposed in the desired position, the inner and outer housings are rotatably tightened together, so that the penetration depth indicator assumes the locked, tightened position firmly and immovably grasping the guide tube. Thereafter, the trocar may be inserted into the patient in the usual fashion with confidence that the depth indicator will remain in the desired position during and after insertion and can be relied upon to accurately indicate trocar tube penetration depth. Advantageously, the distal surface of the outer housing may rest against the patient's skin, as illustrated in FIG. 10.

In a further preferred embodiment, a trocar guide tube positioning skirt is provided for maintaining the position of the guide tube after insertion into the body. Preferably, the guide tube positioning skirt is disposed around the guide tube and adhered to the patient's skin. As will be understood from the following description, the positioning skirt and penetration depth indicator cooperate to prevent inadvertent insertion or withdrawal of the guide tube from the desired penetration depth.

Turning to FIG. 7, there is shown a proximal end view of the positioning device 60 consisting of a clear, generally circular skirt 62 having an axial guide tube aperture 64, a radial slit 66, and a latch member 68. As shown in phantom in FIG. 7, on the distal side of skirt 62 a first annular ring 70 surrounds skirt aperture 64 and a second, circumferential ring is disposed at the outer periphery of the skirt.

As shown in FIG. 8, a cross-section view of positioning device 60 taken along lines 8—8 of FIG. 7, latch member 68 preferably extends from skirt aperture 64 to the outer edge of skirt 62. Skirt aperture ring 70 is disposed adjacent skirt aperture 64 and is adhered to the distal side of skirt 62. Circumferential ring 72 is adhered to the distal side of skirt 62 at the peripheral edge of the skirt. The distal surface of circumferential ring 72 is provided with an adhesive layer 74 covered by a paper release sheet 76.

Figure 9:
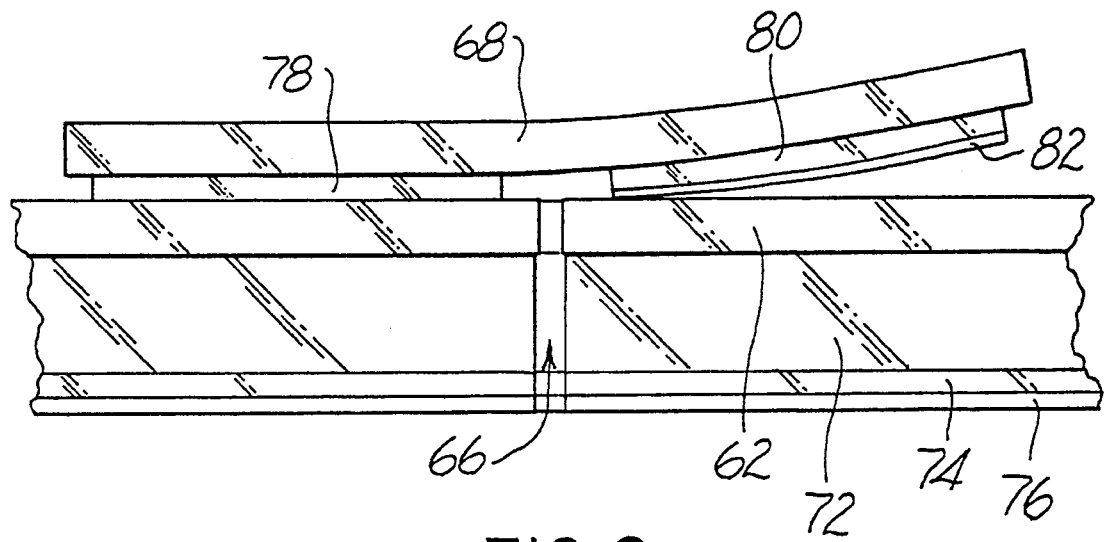
FIG. 9 is a partial elevation view of the guide tube positioning skirt illustrating the latch member.

FIG. 9, a partial elevation view of the positioning device, illustrates the latch member prior to use. As shown, latch member 68 is adhered by an adhesive layer 78 to the proximal surface of skirt 62 on one side of radial slit 66. The portion of latch member 68 extending beyond radial slit 66 has an adhesive layer 80 with a paper release sheet 82 disposed on the side facing skirt 62. FIG. 9 also illustrates circumferential ring 72 with adhesive layer 74 and paper release sheet 76. As shown in exaggerated detail, radial slit 66 extends through circumferential ring 72, adhesive layer 74 and release sheet 76.

Preferably, skirt 62 and latch member 68 are made of a clear plastic material, such as polyurethane or polypropylene. Foam rings 70, 72 may be made of cellular polyethylene. Adhesive layer 74 on circumferential ring 72 should be a medically acceptable adhesive suitable for contacting skin. Adhesive layers 72, 80 on latch member 68 are preferably clear.

After the guide tube is inserted into the patient to the desired penetration depth with the trocar penetration depth indicator in the second, locked position, the positioning device 60 is disposed around the guide tube on the proximal side of the depth indicator by inserting the guide tube through radial slit 66 into axial aperture 6,1. This is readily accomplished since the materials of skirt 62 and rings 70, 72 are sufficiently flexible to be temporarily deformed, as by bending the rings, to permit passage of the guide tube through the radial slit 10 be disposed in aperture 64.

After the guide tube is disposed in skirt aperture 64, release sheet 82 is removed from the latch member and adhesive layer 80 joins latch member 68 to skirt 62 on the second side of slit 66. Thus, the latch member becomes adhered to the skirt on both sides of slit 66 to close off the radial slit and prevent inadvertent removal of the skirt from the guide tube. Release sheet 76 is removed from circumferential ring 72 and the ring is fastened by adhesive layer 74 to the patient's skin.

FIG. 10 illustrates the skirt fastened to the patient's skin, generally designated 100, with foam ring 70 resting on the proximal surface of the trocar penetration depth indicator.

As will be readily appreciated, the trocar penetration depth indicator in the second, locked position disposed against skin 100 prevents the guide tube from further insertion beyond the desired penetration depth. The positioning device disposed in the position shown in FIG. 10, cooperates with the penetration depth indicator to prevent inadvertent withdrawal of the guide tube.

Advantageously, the clear skirt provides visibility of the trocar insertion point during use. In addition, the flexible plastic skirt does not unduly inhibit such side to side movement of the guide tube as may be required by the surgeon to perform any given procedure. Because the materials used to construct the penetration depth indicator and positioning device are relatively inexpensive, the penetration depth indicator and positioning device may be disposable, and may constitute part of a disposable trocar kit.

Figure 11:
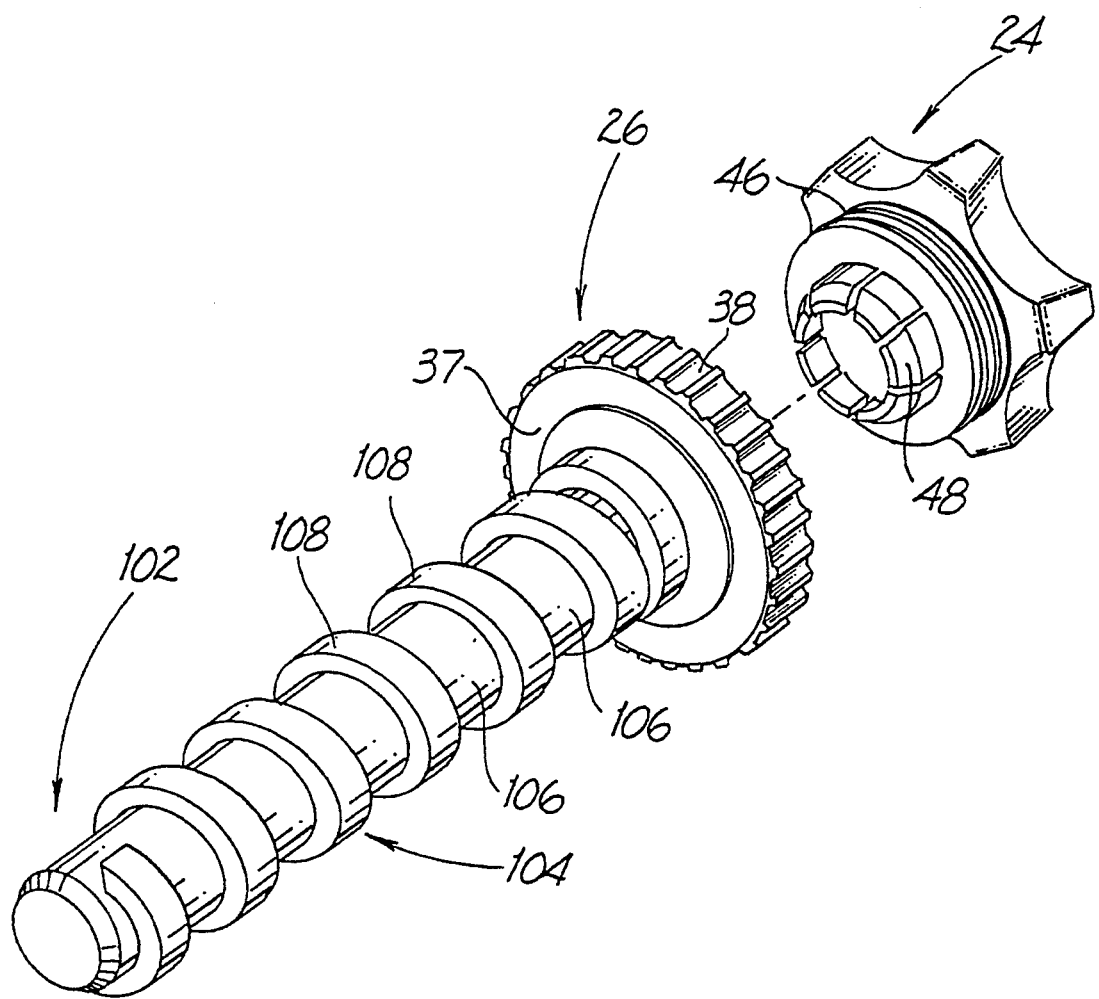
FIG. 11 is a perspective view of an alternative embodiment of the depth penetration indicator and positioning device.

An alternative depth penetration indicator and positioning device configuration is illustrated in FIG. 11. As there shown, second housing 26 includes an integral, distally extending sleeve portion 102 for surrounding the trocar guide tube. Sleeve portion 102 includes radially projecting ribs, shown in FIG. 11 as a helical coil member 104 extending radially from the outer surface of sleeve portion 102. The remainder of the first and second housings 24, 26 are the same as previously discussed. In this embodiment, the depth penetration indicator is mounted on the trocar guide tube and used in the same manner as previously discussed. After penetration, however, sleeve portion 102 is inserted into the incision and helical member 104 engages the skin in order to retain, the trocar guide tube at the desired penetration depth. The sleeve may be inserted into the incision by straight lateral pressure or by turning the depth penetration indicator and/or guide tube to effectively "screw" the sleeve portion and helical member into the skin. Once inserted, the skin surrounds the sleeve and extends into the recesses 106 between the individual ribs or coil segments 108.

To the extent not already indicated, it will be understood by those of ordinary skill in the art that any one of the various specific embodiments herein described and illustrated may be further modified to incorporate features shown in other of the specific embodiments, as desired. By way of example only, it will be understood that the finger gripping depressions may be disposed on the inner housing and the gripping projections on the outer housing, rather than as shown herein. It is also contemplated that the housing distal to the guide tube housing could comprise the inner housing with gripping fingers, in which case the proximal housing would preferably include a nesting area. Furthermore, the shape, configuration and construction materials for the penetration depth indicator and positioning device may be varied, as appropriate. By way of further example, although less desirable, the positioning skirt radial slit may be omitted. Of course, this would require that the skirt be applied to the guide tube before the penetration depth indicator, and might be found to be cumbersome during insertion of the trocar.

The invention in its broader aspects therefore is not limited to the specific embodiments herein shown and described, but departures may be made therefrom within the scope of the accompanying claims, without departing from the principles of the invention and without sacrificing its chief advantages.

What is claimed is:

1. In a trocar guide tube, the improvement comprising a trocar positioning device including
  (i) guide tube gripping means;
  (ii) a guide tube skirt engaging said guide tube gripping means, said guide tube skirt having a distal and proximal side, fastening means for adhering said distal side of said skirt to patient's skin, and a guide tube aperture configured and dimensioned to receive said guide tube, said positioning device further comprising a first pad member disposed on the distal side of said guide tube skirt adjacent said guide tube aperture;
  wherein said fastening means further comprise a second pad member adhered to the distal side of said skirt at the periphery thereof, said second pad member having an adhesive layer on the surface of said second pad member distal to said skirt.

2. The positioning device according to claim 1 wherein said skirt is substantially circular and said second pad member is a substantially circular circumferential ring.

3. The positioning device according to claim 2 further comprising a radial slit through said skirt extending from said guide tube aperture to the edge of said skirt.

4. The positioning device according to claim 3 further comprising a latch member for closing said radial slit.

5. The positioning device according to claim 4 wherein said latch member further comprises a plastic sheet having a first portion adhered to the proximal surface of said skirt on one side of said radial slit and a second portion extending across said slit, said second portion having an adhesive layer and release sheet disposed on the surface thereof facing the proximal surface of said skirt.

6. In a trocar having a guide tube, the improvement comprising a trocar penetration depth indicator and positioning device including:
   (i) a first housing having a proximal and a distal surface, a first engaging portion, a plurality of guide tube gripping fingers, and a substantially cylindrical first housing aperature configured and dimensioned to receive the guide tube with said guide tube fingers extending longitudinally to and surrounding the guide tube;
   (ii) a second housing having a second engaging portion configured and dimensioned to engage said first engaging portion, a second housing camming surface, and a second housing aperture extending axially therethrough and aligned with said first housing aperture to receive the guide tube;
   (iii) said first and second housings assuming a first, unlocked position whereby said first and second housings are axially slidable along the guide tube, and a second, locked position wherein said second housing camming surface exerts radially inward force upon said gripping fingers, such that said gripping fingers frictionally engage said guide tube to prevent axial sliding movement of said first and second housings relative to the guide tube; and
   (iv) guide tube positioning means comprising a skirt member having a guide tube aperture configured and dimensioned to receive said guide tube, a first pad member configured and dimensioned to engage the proximal surface of said first housing, and a second pad member having an adhesive layer for removably attaching said skirt to a patient's skin.

7. The device according to claim 6 further comprising a radial slit through said skirt and first and second pad members.

* * * * *